(12) United States Patent
Marshall (10) Patent No.: US 7,438,418 B2
(45) Date of Patent: *Oct. 21, 2008

(54) MENTAL ALERTNESS AND MENTAL PROFICIENCY LEVEL DETERMINATION

(75) Inventor: Sandra Peery Marshall, San Diego, CA (US)

(73) Assignee: EyeTracking, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/818,260

(22) Filed: Jun. 12, 2007

(65) Prior Publication Data

US 2007/0291232 A1 Dec. 20, 2007

Related U.S. Application Data

(63) Continuation-in-part of application No. 11/361,923, filed on Feb. 23, 2006, now Pat. No. 7,344,251.

(60) Provisional application No. 60/655,843, filed on Feb. 23, 2005.

(51) Int. Cl.
*A61B 3/00* (2006.01)
*A61B 3/14* (2006.01)

(52) U.S. Cl. ............... 351/246; 351/210; 600/558

(58) Field of Classification Search ........... 351/200, 351/203, 205, 209, 210, 246; 702/108, 182, 702/183, 187; 707/101, 104.1; 715/700; 600/544, 545, 558
See application file for complete search history.

(56) References Cited

U.S. PATENT DOCUMENTS

| | | | |
|---|---|---|---|
| 3,691,652 A | 9/1972 | Clynes | |
| 4,012,128 A | 3/1977 | Regan | |
| 4,931,865 A | 6/1990 | Scarampi | |
| 5,280,793 A | 1/1994 | Rosenfeld | |
| 5,331,969 A | 7/1994 | Silberstein | |
| 5,564,433 A | 10/1996 | Thornton | |
| 5,617,872 A | 4/1997 | Scinto et al. | |
| 5,620,436 A | 4/1997 | Lang et al. | |
| 5,632,282 A | 5/1997 | Hay et al. | |
| 5,649,061 A | 7/1997 | Smyth | |
| 5,651,107 A | 7/1997 | Frank et al. | |

(Continued)

FOREIGN PATENT DOCUMENTS

AU  5865600 A  10/2000

(Continued)

OTHER PUBLICATIONS

"A Gaze-Responsive Self-Disclosing Display"; Starker et al.; CHI '90 Proceedings, Media Lab, Massachusetts Institute of Technology (Apr. 1990).

(Continued)

*Primary Examiner*—Mohammed Hasan
(74) *Attorney, Agent, or Firm*—Miintz, Levin, Cohn, Ferris, Glovsky & Popeo, P.C.

(57) ABSTRACT

A method for determining mental proficiency level by monitoring point of gaze, pupillary movement, pupillary response, and other parameters in a subject performing a task, collecting the data in a database, analyzing the data in the database, and assigning the subject to a score indicating the subject's particular mental proficiency level in real time.

20 Claims, 4 Drawing Sheets

U.S. PATENT DOCUMENTS

| | | | |
|---|---|---|---|
| 5,704,369 | A | 1/1998 | Scinto et al. |
| 5,724,987 | A | 3/1998 | Gevins et al. |
| 5,886,683 | A | 3/1999 | Tognazzini et al. |
| 5,963,300 | A * | 10/1999 | Horwitz ............... 351/209 |
| 5,982,555 | A | 11/1999 | Melville et al. |
| 6,024,707 | A | 2/2000 | Scinto et al. |
| 6,067,565 | A | 5/2000 | Horvitz |
| 6,070,098 | A | 5/2000 | Moore-Ede et al. |
| 6,090,051 | A | 7/2000 | Marshall |
| 6,102,846 | A | 8/2000 | Patton et al. |
| 6,102,870 | A | 8/2000 | Edwards |
| 6,106,119 | A | 8/2000 | Edwards |
| 6,572,562 | B2 | 6/2003 | Marshall |
| 6,712,468 | B1 | 3/2004 | Edwards |
| 7,029,121 | B2 * | 4/2006 | Edwards ............... 351/246 |
| 2001/0011211 | A1 | 8/2001 | Bushey et al. |
| 2002/0015064 | A1 | 2/2002 | Robotham et al. |
| 2002/0107972 | A1 | 8/2002 | Keane |
| 2003/0038754 | A1 | 2/2003 | Goldstein et al. |
| 2003/0069616 | A1 | 4/2003 | Skene |
| 2003/0078513 | A1 | 4/2003 | Marshall |
| 2003/0225591 | A1 | 12/2003 | Clay et al. |

FOREIGN PATENT DOCUMENTS

| | | |
|---|---|---|
| EP | 1164919 A1 | 1/2002 |
| EP | 1164919 A4 | 5/2003 |
| WO | WO99/18842 | 4/1999 |
| WO | WO00/54654 | 9/2000 |
| WO | WO/2004/084117 | 9/2004 |

OTHER PUBLICATIONS

"Development of Predictive Chi with Eye Movements"; Takagi, H.; Master Thesis, University of Tokyo (Feb. 7, 1996).

"The Index of Cognitive Activity: Measuring Cognitive Workload"; Sandra P. Marshall; In Proceedings of the 2002 IEEE 7th Conference on Human Factors and Power Plants; New York: IEEE;.7.5-7.10.

"Eye Tracking in Advanced Interface Design;" Jacob, R.; Human-Computer Interaction Lab, Navel Research Lab, Washington, D.C.; www.eecs.tufls.edu/~jacob/papers/barfield.html.

"Integrating Psychophysiological Measures of Cognitive Workload and Eye Movements to Detect Strategy Shifts"; Marshall et al.; Proceedings of the 36th Annual Hawaii International Conference on Systems Sciences, Los Alamitos, CA: IEEE; Jan. 2003 (6 pages).

eyetools™ home page; http://www.eyetools.com; printed Feb. 21, 2006.

Ahern and Beatty, Science (1979) 205:1289-1292.

Bradshaw, Quarterly Journal of Experimental Psychology (1968) 20:116-122.

Davidson and Sutton, Current Opinion in Neurobiology (1995) 5:217-224.

Gardner et al., Perceptual and Motor Skills (1975) 41:951-955.

Granholm et al., Psychophysiology (1996) 33:457-461.

Hess and Polt, Science (1964) 140:1190-1192.

Kim et al., Cortex (1998) 34:753-762.

Lowenfeld, in The Pupil: Anatomy, Physiology and Clinical Applications, vol. 1; Ames, Iowa, Iowa State Univeristy (1993) pp. 83-89.

Metalis et al., Journal of Applied Psychology (1980) 65:359-363.

Schluroff, Brain and Language (1982) 17:133-145.

Wierwille et al., "Research on vehicle-based driver status/performance monitoring: development, validation, and refinement of algorithms for detection of driver drowsiness" National Highway Traffic Safety Administration Final Report: DOT HS 808 247, VPISU Report No. 94-04, Dec. 1994.

Wierwille, et al., "Research on Vehicle-Based Driver Status/Performance Monitoring, Part III", USDOT HS 808 640, Sep. 1996.

Tijerina, et al., "A Preliminary Assessment of Algorithms for Drowsy and Inattentive Driver Detection on the Road", USDOT HS 808 (TDB) Mar. 1999.

* cited by examiner

MENTAL ALERTNESS AND MENTAL PROFICIENCY LEVEL DETERMINATION

RELATED APPLICATIONS

This application is a continuation-in-part of U.S. patent application Ser. No. 11/361,923, filed Feb. 23, 2006 now U.S. Pat No. 7,344,251, which in turn claims the benefit of priority of provisional application Ser. No. 60/655,843, filed Feb. 23, 2005, the contents of both are hereby fully incorporated by reference.

BACKGROUND

As today's workplace becomes increasingly sophisticated and technologically complex, workers are experiencing ever increasing demands on their competence, awareness, and abilities. Workers increasingly rely on technologically complex equipment to support proper workplace functioning. Moreover, the workers, as operators of this equipment, must function efficiently and safely at every moment. In particular, the level of mental proficiency of the operator is of vital importance: Is the operator performing within expected guidelines for a particular task? Knowing the mental proficiency level of the operator at any moment would allow the operator's supervisor or the equipment itself to know if the operator is at a level that may decrease productivity or pose a safety risk. Either the technology itself or the operator's supervisor could then raise an alarm and take appropriate action such as relieving the operator or providing additional support.

SUMMARY

In one aspect, eye tracking data characterizing pupil and point of gaze for an individual can be obtained. Thereafter, the data is associated with one or more of a plurality of predefined mental proficiency levels to allow for the associated predefined mental proficiency level to be determined. In some variations, the eye tracking data is analyzed using a discriminant function analysis. In other variations, the eye tracking data is analyzed using a non-linear classification analysis or procedure.

The plurality of predefined levels of mental proficiency can be generated by providing a controlled setting characterized by one or more levels of mental proficiency, subjecting one or more test individuals engaged in a task to the controlled setting, obtaining eye tracking data from the test individuals, performing calculations on the eye tracking data, and modeling the eye tracking data to describe the one or more levels.

The level of mental proficiency to be measured can be selected from any group that characterizes proficiency level including, without limitation, novice, intermediate, expert, and the like. The mental proficiency levels may vary based on the underlying job, task, or activity (e.g., driving a vehicle, performing surgery, performing a visual search task, etc.).

The eye tracking data can comprise one or more of pupil size, direct eyelid measurements such as vertical separation of the upper and lower eyelids and/or rate of eyelid movement, vertical location of the pupil, and horizontal location of the pupil. The eye tracking data can be collected at a frequency of up to about 1000 observations per second.

The eye tracking data can be subjected to an analysis comprising one or more of calculating an Index of Cognitive Activity (ICA), calculating a blink rate, calculating a movement of the pupil in a horizontal and in a vertical plane, and calculating a divergence of the horizontal location of the pupil.

The eye tracking data collection and analysis can occur in real time or the data analysis can be performed on pre-existing data (based on previously recorded and stored eye tracking data). In addition, in some variations, the eye tracking data can be monitored in the eyes of one or more individuals so that in some implementations, mental proficiency level of one or more individuals can be reported.

In another aspect, eye tracking data characterizing pupil dilation and point of gaze for each eye of an individual is obtained. Metrics based on the data can be calculated such as index of cognitive activity (ICA), blink rate, rate of pupil movement, rate of change of point of gaze, and divergence between the point of gaze for each eye. These metrics can then be associated with one or more of a plurality of predefined levels of mental proficiency to allow for the identification of the associated predefined mental proficiency level.

Articles are also described that comprise a machine-readable medium embodying instructions that when performed by one or more machines result in operations described herein. Similarly, computer systems are also described that may include a processor and a memory coupled to the processor. The memory may encode one or more programs that cause the processor to perform one or more of the operations described herein.

The details of one or more variations of the subject matter described herein are set forth in the accompanying drawings and the description below. Other features and advantages of the subject matter described herein will be apparent from the description and drawings, and from the claims.

DESCRIPTION

An operator performing a task can be monitored unobtrusively by a remote camera capable of recording important eye tracking data such as pupil dilation, eye movements and fixations, and blinks. The eye data can be processed, for example in real time, to provide an estimate of the current level of mental alertness or mental proficiency.

A difficulty in estimating the level of mental alertness or mental proficiency (i.e., level of cognitive awareness or cognitive state) an operator is in at any given time is that such levels are not discrete entities with identifiable boundaries that can be uniquely and absolutely determined. Rather, there exists a continuum of mental alertness ranging from the low end (e.g., drowsiness/fatigue) to the high end (e.g., overload/stress). A similar continuum exists for mental proficiency, ranging from low (e.g., novice) to high (e.g., expert). Any number of levels may be identified along this range. For example, the following alertness levels may be specified: drowsy/fatigued; bored; engaged; distracted; overloaded/stressed; impaired (for example, by psychoactive substances such as drugs or alcohol). These are a potential set of levels of mental alertness. Other alertness levels may also be defined. Similarly, any number of levels of mental proficiency may be identified. For example, the levels might be: novice, intermediate, advanced, beginner, competent, proficient, expert, and the like. Other proficiency levels may also be defined.

These levels may not necessarily form a linear continuum reflected by any single measurement or metric. However, the totality of the metric information produced by a linear or nonlinear multivariate statistical model may be used to distinguish the levels.

The levels of interest may be determined by the specifics of any workplace or other environment in which monitoring is desired. Some mental alertness levels that have been previously identified and monitored in numerous studies are drowsiness and distraction. In many situations, it may be necessary to monitor the operator's level of drowsiness (e.g., operators of heavy machinery, truck drivers, air traffic controllers, nuclear power plant operators). Several techniques have been used in this effort. For instance, many systems use a camera to register the closure of the eye. The technique cited most often involves the PERCLOS metric, which measures the extent to which the eyelid covers the pupil over an extended period of time. When the PERCLOS measure reaches a predetermined level—often the proportion of time in one minute that the eye is at least 80% closed—the individual is deemed drowsy. When the PERCLOS measure reaches a predetermined level, the individual is deemed drowsy. Unfortunately, this measure can only sound an alarm after individuals are so drowsy that they cannot keep their eyes open. Safety is already compromised by that time.

Few physiological measures are available that capture the upper end of mental alertness or mental proficiency. In 1999, the Index of Cognitive Activity (ICA) was developed and patented as a method of measuring cognitive workload. (See, for example, U.S. Pat. No. 6,090,051.) The ICA was designed to assess levels of cognitive activity, and many studies using different tasks have validated that the ICA increases for tasks requiring high levels of mental alertness and/or proficiency and decreases for tasks requiring low levels.

The ICA is based on measurement of changes in pupil dilation. As effortful cognitive processing occurs, the pupil reacts with sharp, abrupt bursts of dilation. These dilations are very small and very frequent. When little processing occurs, they are absent. The ICA processes the pupil signal, removes the artifacts created by eye blinks, and measures the changes in pupil dilation.

The difficulty in processing the many types of eye tracking data is that the relevant events occur on very different time scales. For example, significant changes in pupil dilations may be measured by milliseconds, changes in blinks by seconds, and changes in very long fixations by tens of seconds. The subject matter described herein allow for a wide variety of eye metrics into a common time framework. That framework then forms the basis for statistical estimation and prediction of level of mental alertness or proficiency in real time for any operator on any task. The task does not have to be known in advance nor do the actions of the operator need to be known.

As the ICA demonstrates, information derived from the eyes may be extremely useful. But, obviously, more information is available than just pupil size alone. Would the inclusion of other information such as eye movement or blinking make it possible to detect a wider range of mental alertness levels? The answer is yes, and the subject matter described herein may be used to estimate mental alertness or proficiency levels from a set of eye metrics—for example, metrics based on pupil dilation together with horizontal and vertical position of the point of gaze. Pupil dilation refers to any change in pupillary diameter which occurs in a subject's eye. Point of gaze refers to any point of reference upon which a subject's eye focuses (for example, a visual display) for a measurable period of time.

Furthermore, the subject matter described herein is based on psycho-physiological data plus the presence or absence of eye movement. Specification of the nature of the eye movement (such as location, direction, speed) is not necessary in some variations.

Data on eye tracking is collected using a camera capable of capturing information at a suitably high rate. The most basic eye data are recordings taken at a fixed sampling rate. The raw eye tracking data comprise recordings taken, for example, at 4 msec intervals (i.e., samples at 250 Hertz (Hz)). The data consist of, for example, three fundamental measurements: the size of the pupil, and the vertical and horizontal location for each eye. Specifically, the vertical and horizontal measurements can be reported, for example, relative to the point of gaze directed at a computer screen. A "0,0" pixel can be determined, for example, and the relative position (horizontal and/or vertical) of the point of gaze can then be reported.

From these three measurements (for example) all other metrics of interest may be derived, including blinks (including eyelid opening and/or closing speed), fixations, and rapid intermittent eye movements, such as those occurring when the eyes move from one point to another in the visual field, known as saccades. In addition, several other metrics may also be computed, such as eyelid opening and/or closing speed, vertical eyelid separation distance, or other direct measurements of eyelid motion or separation, and, in some variations, these metrics are useful in predicting level of mental alertness. Furthermore, metrics characterizing blinks may also involve pre- and post-blink eyelid movement as well as partial blinks.

Figure 1:
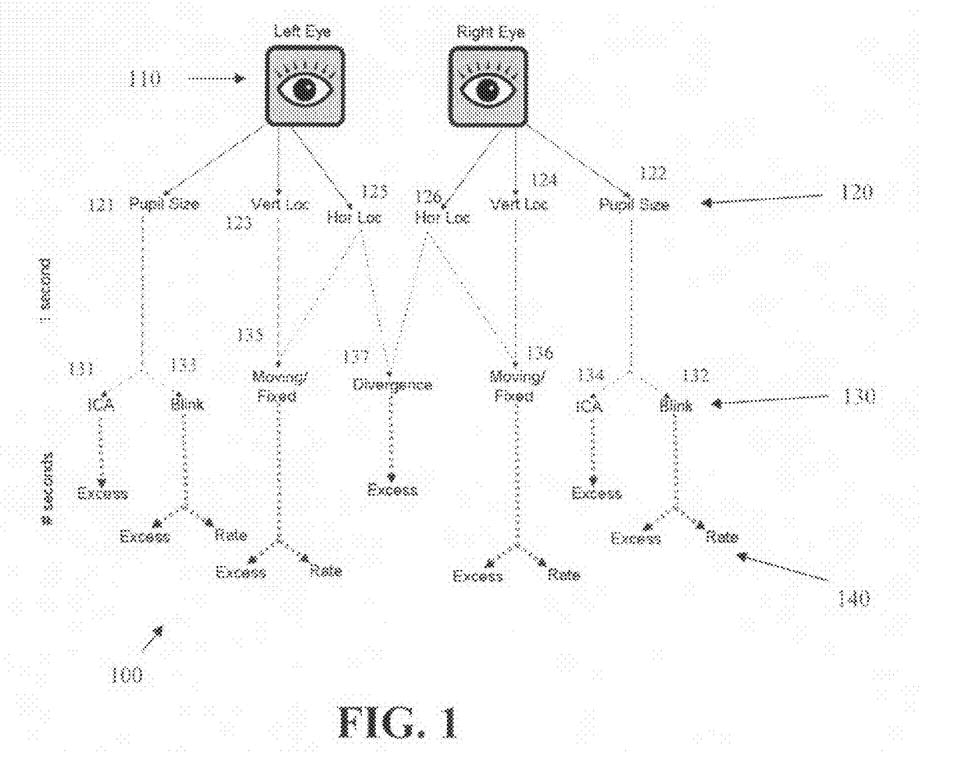
FIG. 1 is a flowchart characterizing data collected from each eye and subsequent analyses of such data.

FIG. 1 provides a sample illustration 100 of the constitutive elements of various metrics. A camera, for example, collects data from the subjects left and right eyes 110. The basic measurements 120 of pupil size 121, 122 and vertical 123, 124 and horizontal location 125, 126 may occur every 4 milliseconds. When a predetermined, sequential number of these measurements are available, such as 250 observations in one second, additional metrics may be computed. These intermediate metrics 130 are shown in the middle portion of FIG. 1 and include blinks 132, 133, eye movement 135, 136, the ICA 131, 134 (see below), and divergence 137 (see below). Finally, after some longer period of time (such as 10 or 15 seconds), final metrics 140 may be computed. These final metrics may consist of rates such as how often blinks occur, how often and what type of eye movement occurs, and how often excessive values of divergence or fixated eye position occur, and the like.

Many of the measurements and metrics in FIG. 1 may be computed in real time—the measurements 120 and intermediate 130 and final 140 metrics may be calculated in 1 second or less with conventional computing resources. Others metrics may demand additional time because they are defined by how often they occur over some period of time. In some variations, data may be collected and analyzed in real time for about one minute before a formal period of observation. With this arrangement, all the metrics may be presented in real time because there exists a time buffer of the appropriate length upon which to base the rate measures.

Each of the metrics shown in FIG. 1 may provide unique information that can be valuable in predicting mental alertness level. Brief descriptions are provided below for the intermediate set 130 comprised of: Index of Cognitive Activity (ICA) 131, 134; Divergence (D) 137; Blinking (B) 132, 133; and Movement (M) 135, 136.

Index of Cognitive Activity (ICA) 131, 134. The Index of Cognitive Activity (ICA) is a method that uses pupil diameter (i.e., pupil size 121, 122) to estimate cognitive workload. One method for obtaining the ICA is wavelet analysis. (For example, see col. 9, 1. 28 through col. 14, 1. 56 of U.S. Pat. No. 6,090,051.) The ICA 131, 134 measures brief bursts of activation that occur in the muscles that govern pupil expansion. These bursts may occur during periods of effortful cognitive processing. Calculation of the ICA 131, 134 requires multiple observations and may, for example, be based on the number of measurements taken in one second (usually 60 or 250). However, other time lengths could be chosen as long as they were sufficient for calculation the wavelets that underlie the ICA 131, 134 derivation. An important property of the wavelet analysis that creates the ICA 131, 134 is that it yields the same values for any subset no matter where the calculation starts. This feature means that it is possible to examine the whole signal or any part of it with no loss of information or change in value.

Calculation of the ICA 131, 134 yields not only a second-by-second estimate of level of mental alertness, it may also result in a binary vector having the same length as the original pupil signal. The non-zero elements of this vector may indicate the times at which unusual pupil activity occurred and hence are indicators of mental effort.

The ICA 131, 134 is typically computed as the sum of the binary vector for each second of interest. The average ICA 131, 134 may be then computed across the entire period of observation or each second's ICA 131, 134 may be desired. Both measures may be further transformed by the hyperbolic tangent in order to create output within the range of 0-1.

Divergence (D) 137. Eye divergence (D) 137 may be computed by measuring the horizontal location of both left 125 and right 126 eyes, and finding the absolute difference between the two. The measurement may, for example, be taken every 4 msec. When an individual maintains focused attention on a feature, event, or task, the left and right points of gaze are very close together if not overlapping. When attention is lost, these points of gaze tend to separate, as focus shifts from the target to some very distant point. D 137 may, for example, be measured per second to yield average distance between the two points of gaze. It may also be averaged to determine the mean divergence across the entire time period of measurement.

Blinking (B) 132, 133. The eye is typically in one of three states: blinking, moving, or fixating. Blinking 132, 133 refers to eyelid closure, either full or partial. Blinks 132, 133 vary in duration. It is well known that very long blinks 132, 133 are indicative of drowsiness, whereas very short blinks 132, 133 are often indicative of sustained attention. Most blinks 132, 133 last less than 1 second, although longer blinks 132, 133 may be recorded. The calculation of blinks 132, 133 may require multiple observations, and real-time computation may necessitate use of a variable time interval that continues until the blink 132, 133 has terminated. Blinking 132, 133 may be calculated, for example, as the number of observations involved in a blink 132, 133, with observations taken at a sampling rate of 4 msec. Blinks 132, 133 are not simply zero recordings of pupil size because there are substantial changes in pupil diameter during the initiation and conclusion of each blink 132, 133. These changes may be magnified during drowsiness because the eyes become "heavy" and closure/opening may take extended periods of time. Partial blinks 132, 133 also occur in which the eyelid partially occludes the pupil. For analysis purposes, the number of observations per second that are considered to be part of a blink 132, 133 may be calculated. This value may be transformed by the hyperbolic tangent function to fall within the range of 0-1. It should be noted that data characterizing blinks 132, 133 can be obtained in a variety of ways, including direct measurement of eyelid movement or separation (e.g., the distance from the top lid to the bottom lid at any given time), as noted above.

Moving (M) 135, 136. If the eye is not engaged in blinking, it is either moving or fixed 135, 136. Measurement may, for example, be made of the location of each eye every 4 msec. When that location changes from one measurement to the next by more than a specified amount (such as moving more than one pixel width in any direction on some screen displays or such as exceeding a velocity threshold), the eye is said to be moving. The number of observations per second during which movement is detected may be recorded. This value may be transformed by the hyperbolic tangent function to fall within the range of 0-1.

Figure 2:
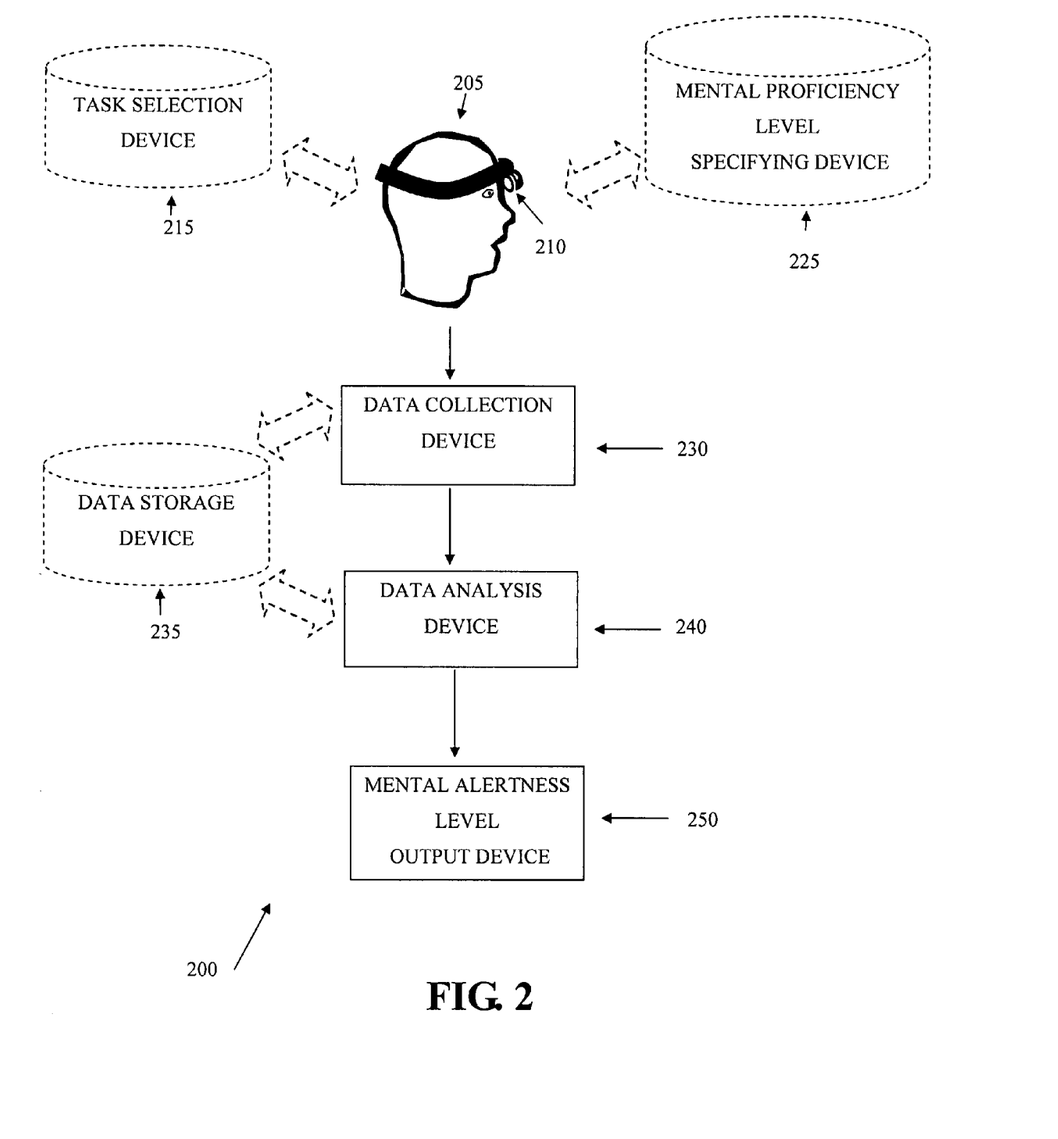
FIG. 2 is process flow diagram of data collection, analysis, and reporting.

FIG. 2 depicts a process flow diagram 200 of the system and method for pupillary monitoring, and the data collection 230, analysis 240, and determination and reporting of the level of mental alertness 250 in a subject 205. The following various steps that may be used singly or in combination to facilitate the determination of the level of mental alertness or mental proficiency. Additionally, apparatus may also be used that includes components that provide one or more of the following functions.

Task selection 215. Typically, mental alertness or proficiency level identification and prediction will occur when an individual is working on a defined job, task, or activity. Task selection may be open ended, such as monitoring an individual whenever he is considered to be on the job, such as the workday of a nuclear power plant operator, or it may, for example, be specific, such as monitoring an individual during a constrained period of time, such as a 30-minute shift of an airport security screener. This step 215 is optional and thus shown in dashed lines.

Specify number of levels of mental alertness or mental proficiency 225. Many situations will contain at least two levels of interest: overloaded and fatigued, for example, or novice and expert. Other levels such as bored or attentive may also be of interest. The circumstances of the situation may dictate the number of levels to be modeled.

An inspection of the task(s) may indicate which levels may be elicited. However, mental alertness or proficiency level specification is not a required step, and the subject matter described herein may be useful even if the levels of mental alertness or mental proficiency are unknown; thus, this step is shown in dashed line 225. In such cases, techniques such as unsupervised learning in a neural network (see below) may be implemented. The principle drawback of unsupervised learning is that it is often inefficient. It may be necessary to try several configurations and several numbers of distinct states or levels before a solution is reached.

Collect and analyze data 230, 240. As the subject's pupils are monitored, the resultant data is collected 230 and analyzed 240. Analysis of level of mental alertness requires data, either pre-existing data or current real-time data. Eye tracking data may comprise computer records of measurements taken by camera 210 at a specified sampling rate. Typical rates are 60 Hz and 250 Hz, but other rates (e.g., 4 Hz or 1000 Hz) are possible. Some eye tracking systems record data from both eyes and other record data from a single eye. The subject matter described herein applies to any sampling rate and to one-eye or two-eye systems equally well, although some of the metrics may not be available under all eye tracking configurations. In those instances, subsets of the metrics may provide the best available information.

Eye tracking systems provide the raw data of, for example, pupil measurement and horizontal/vertical position of the eye(s). Other data provided by eye tracking systems include measurements of eyelid movement or distance between the upper and lower lids over time. These data may be analyzed 240 in real time or stored in some electronic storage system 235 (shown in dashed lines to indicate the optional nature of this system) for later analysis.

Figure 3:
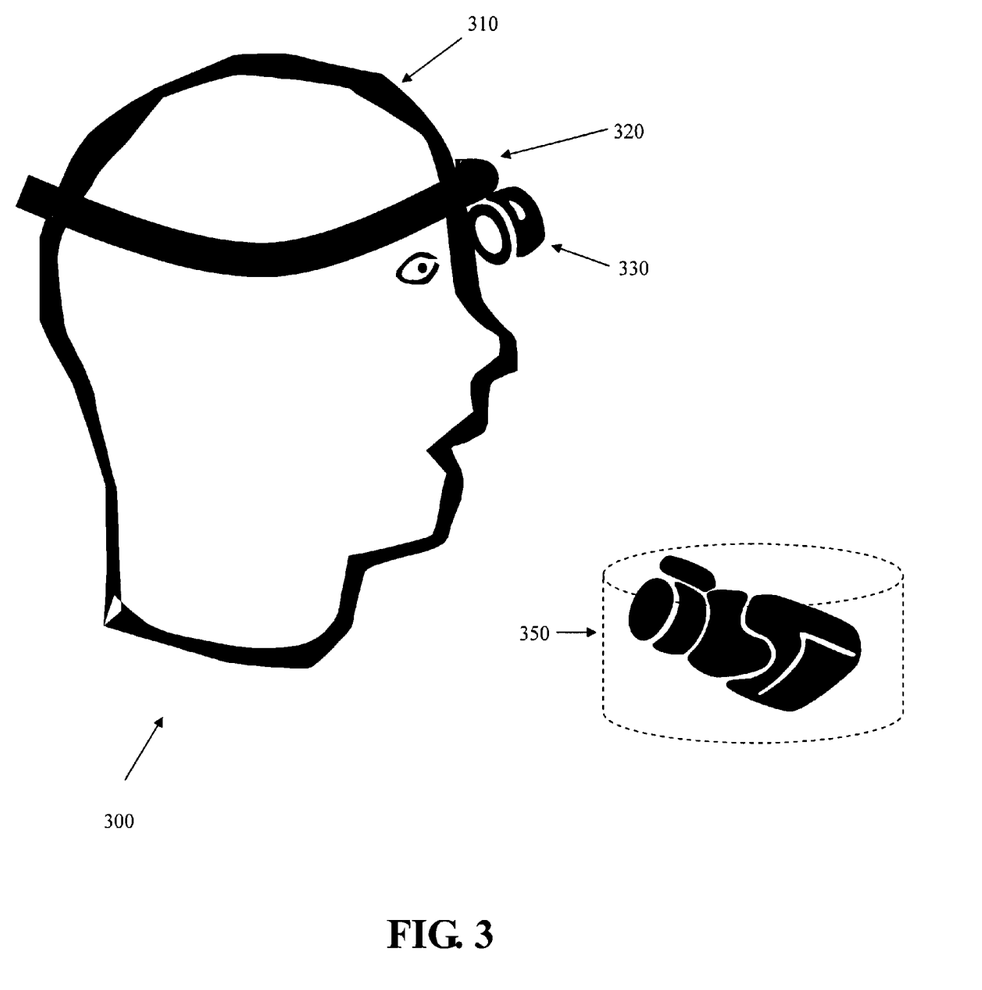
FIG. 3 is a diagram demonstrating possible equipment configurations for data collection.

FIG. 3 depicts an exemplary system for monitoring pupillary information and collecting eye tracking data. Eye tracking systems currently exist as head-mounted optics (e.g., FIG. 2 at 210 or FIG. 3 at 330), in which the individual 310 wears either a headband 320 or helmet with cameras 330 attached, or they exist as remote systems, placed typically in front of the individual at a distance of about 18-24 inches 350 (shown in dashed lines as an optional feature). The nature of the hardware is not a limiting factor for the subject matter described herein. As long as the eye tracking system is accurate and has reasonable resolution, the subject matter described herein may be applied.

Compute eye metrics. The analysis 240 may take raw data or measurements from an eye tracking system and process it to produce second-by-second values for a number of eye metrics. The process flow diagram 100 of FIG. 1 demonstrates seven such eye metrics: ICA (left 131 and right 134 eye), blinks (left 133 and right 132 eye), movement (left 135 and right 136 eye), and divergence 137. A counting variable that indicates the number of seconds being processed may also be included as a placeholder for elapsed time. The unit of measurement may, for example, be one second. The frequency of observations (i.e., number of observations per second, reported at Hz varies. For example, 60 and 250 Hz, as well as 4 Hz and 1000 Hz, systems are useful. This unit (Hz) is selected for simplicity and familiarity; any time unit can be used in its place.

For real-time computation, determination of the eye metrics may require a one-second lag behind real-time performance so that sufficient data may be captured to make the computations. Lags of one second are generally not considered to be burdensome in real situations because decisions are rarely made at one-second intervals. The result of this step is a vector of eye metrics having k elements, where k may range between 1 and 7, for example, depending on the number of metrics available.

For computation of previously stored data, the same computational procedures may be implemented. Data is chunked by the appropriate number of observations, and the metrics may be computed. The result here is a matrix of data for each individual of size n-by-k, where n is the number of seconds over which the metrics are computed and k is the number of metrics as described above for real-time computation. Each row is a 1-by-k vector of metric data for a specific second.

Identify mental alertness or mental proficiency level.

Analysis of the metrics can proceed along many different paths. Two such paths are discriminant function analysis and neural network analysis (a type of adaptive or self-learning analysis). Discriminant function analysis (also called discriminant analysis) is a statistical procedure that derives linear combinations of a set of variables in order to discriminate among pre-defined states or levels. The calculations are made under the constraint that the misclassification error rates are minimized. For the detection of two levels of mental alertness, discriminant function analysis takes the data for a single individual and finds the linear function that best separates the seconds of performance into two groups (corresponding to the two levels of interest). The classification is based only on the eye metrics and is computationally similar to the statistical procedure of multiple regression analysis. A high success rate of classification means that the eye metrics successfully predict the underlying level of the task for a particular individual. A low success rate means that they do not. For multiple mental alertness or mental proficiency levels, the statistical analysis is more complex and yields multiple discriminant functions that altogether capture the differences among the categories to be classified.

A non-linear classification procedure, such as neural network analysis, has a similar objective—to classify the seconds of performance into two defined outcomes. A main difference between the two statistical approaches is that the neural network is nonlinear. The network has three layers: input, hidden, and output. The number of input units depends upon the number of elements in each data vector (e.g., the exemplary 7 for eye metrics, as mentioned above). The number of hidden units varies according to the complexity of the function to be modeled. The number of output units corresponds to the number of classification categories (i.e., number of levels of mental alertness or mental proficiency).

Training proceeds by sending information from the input layer to the output layer through the hidden layer. Feedback goes the other way: from output layer to input layer via the hidden layer. Each node at each layer is connected to every node at the layer immediately above as well as the layer immediately below it. Random weights are given to all connections to initiate training. Training occurs by processing single vectors of data at a time successively. For any vector, each input node will pass its value to each hidden unit, with each value weighted appropriately by the value of its connection. Once the output units have received their full input from the network, the node having the highest value is considered to be the winner. If this node does not represent the correct classification, the network may automatically send a correction back down all the connections to adjust the weights. This modification can be done after each vector is processed or, more commonly, after all vectors have been presented to the network. The set of vectors is repeatedly given to the network for processing until some statistical threshold is reached. A typical threshold is mean square error, the average squared error between the outputs and the target classifications.

One training algorithm used is, for example, the Levenberg-Marquardt algorithm for backpropagation, with a tan-sigmoid transfer function in the hidden layer and a linear transfer function in the output layer. A second algorithm is steepest gradient descent with momentum.

Unsupervised learning in a neural network refers to the absence of known outputs. Only the inputs are known, and the mathematical algorithms for this process aim to cluster and reduce the inputs into sets of similar vectors. The underlying statistical techniques are based on feature detection (looking for similarities among inputs) or on density estimation (underlying processes that generated the inputs). As the similarities among inputs are recognized, they can be compared to baseline models or measurements to identify, for example, the level or levels of mental alertness of interest. The following examples will help clarify this.

EXAMPLE I

When a full matrix of data for an individual is already computed and the level identification is known for the task, the data may be processed by any statistical classification technique such as multiple discriminant function analysis or neural network analysis. In these instances, the task levels may serve as the class categories. Each technique may assign weights to the data of a row vector and may assign that vector to a single category (i.e., makes a level determination for that vector). For tasks that are well defined and designed to elicit a single level, data collected across multiple tasks should result in classifications in which most of the seconds from any specific task point to a single level.

For tasks that are not well defined, several levels might have significant numbers of seconds for which they were identified. For example, an individual might be attentive for a while, and the row vectors for that phase of the task may point to the mental alertness level of attentive. But, the individual could then become bored by the task. This bored condition would be a second phase of the same task, and now the row vectors should point to a different mental alertness level of boredom. Because each second may be uniquely identified by its time counter, it may be determined whether the bored level truly corresponds with a period of boring activity during the task.

EXAMPLE II

When a full matrix of data for an individual is already computed and the level identification is not known, a technique such as unsupervised learning in neural network analysis may be used. (See above.) For such situations, the technique may perform various clustering operations in order to detect a finite number of classification levels.

EXAMPLE III

When data analysis occurs in real time, only a single row vector at a time may be available for analysis. The same general procedures described for Example I or Example II apply with a few modifications. First, it is often possible to collect a baseline sample of data for a period of time prior to the real-time data collection. This baseline sample may be analyzed as a whole, using the techniques from Example I or Example II (i.e., either with levels known or unknown). The results may be a set of statistical weights that may be applied to each new row vector as it emerges in real time, and the classification can be made for that single second of data.

A second way to aggregate the data is to average the vector information over a fixed interval (such as 5 seconds) and then apply the weights to the averages. In this case, only a single level determination is made for the entire interval. This method of aggregation is especially appropriate for multi-level detection.

EXAMPLE IV

When data analysis occurs in real time and no baseline analysis has been done, analysis may proceed in several ways. Most often, it will be useful to take the results of some previous collection of analyses (i.e., many individuals over the same task or the same individual at an earlier time) and normalize them. These analyses may have used prior knowledge of specific levels or may have determined the levels from the clustering technique described in Example II. The resulting statistical weights may then be applied. Alternatively, one may compute additional statistics over the metrics as the real-time analysis proceeds and may use these statistics for determining different levels. For example, one could monitor the ICA and/or divergence over 10 seconds and compute the average. Continuing to do this would produce a new vector of moving averages. Change in slope over time in this vector may be considered a level change.

For any individual in all four examples described above, once the analysis has been concluded, the values obtained in the analysis may be used for subsequent analysis of additional data collected from that individual. An individual may be tested on several well-defined levels to obtain appropriate statistical parameters for the technique being used. These parameters may serve as baseline data. Then, the target task (s) may be given to the individual without further predetermination of expected level of mental alertness or mental proficiency, and the parameters may be used to estimate which levels were evoked by different parts of the task(s).

The above steps may produce second-by-second estimates of mental alertness or mental proficiency level that are made as the individual performs a dynamic task that generally varies along multiple features. The accuracy of the classification will generally improve if the results are aggregated over a longer period of time. For example, if we take a 5 second average and add the rule that at least 4 of the 5 seconds should have a common classification, the overall accuracy increases because the occasional lapse is removed. In some variations, systems designed to estimate an operator's workload level may do so on a much longer time basis such as 15 seconds or even on a minute-by-minute basis. When the procedure is extended to these longer time standards and moderate rules are applied such as having at least 75% of the classifications be consistent, accuracy approaches 100%.

With a longer time frame for analysis, additional variables shown in the third layer of FIG. 1 may be incorporated. These may, for example, include measures of rate for blinks and movements. They may, for example, also include measures that are defined as excessive, meaning very long blinks, very large divergence, very high ICA, and very long periods of stability and/or movement. The steps above may be repeated with the aggregates for the original metrics if desired, coupled with the new metrics for the appropriate time period. For example, assume that data is to be analyzed on the one-minute basis for some period of time such as one hour. The metrics used in the example above may be computed for averages across each minute, and the additional metrics of rate and excess would be derived from them. The full set may then become the basis for level analysis.

Once the level has been determined, action may be taken on the basis of that level, starting with the outputting of the level determination (see FIG. 2 at 250). For example, the subject's (see FIG. 2 at 210) supervisor is alerted to a subject who has become drowsy and the supervisor takes action to arouse the subject. In another example, the output of the mental alertness level determination goes to a device that then alerts the drowsy subject, for example, using a horn or tactile alarm, for example.

A specific example of selecting a task, selecting mental alertness levels of interest, collecting data, computing metrics, and determining an operator's mental alertness level involves driving a car. Using a driving simulation program presented on a computer monitor, operators complete basic lessons which had them driving through urban and suburban environments, dealing with traffic lights, signs, posted speed limits, schools, and other traffic. The operators complete several episodes of driving and several episodes of driving while doing additional tasks, each episode lasting 2-4 minutes.

This example looks at two distinct levels of mental alertness: focused attention (during driving only) and potential overload (with the imposition of the additional tasks while driving). To test whether the observed data corresponds to two distinct levels, all seconds of performance are given a binary code, with the seconds during the driving only episodes coded '0' and the seconds during the math added episodes coded '1.' The data from each episode are combined for each operator and are analyzed to determine whether the eye metrics could reliably estimate the level of mental alertness coding.

Both data sets are analyzed in two ways: first with a linear discriminant function and second with a nonlinear, back-propagation neural network analysis. With only two categories of classification, the discriminant function analysis yielded a single function which was statistically significant in all cases. The neural network is a 3-layer network with 7 inputs (the metrics), 7 hidden units, and 2 output units. Separate analyses using each technique are done for each participant.

The results show that the metrics based on eye tracking data accurately describes the level of mental alertness of the operator. On the basis of only 5 seconds of data, the level of mental alertness can be correctly predicted more than 75% of the time. And, when limited to a single second, the classification rate drops only five percent, yielding a still useful 70%.

Another specific example of using eye tracking data to measure mental alertness levels involves problem-solving. The problem solving example uses two conditions. In one condition, a participant is asked to solve a set of arithmetic problems which are presented orally at 10 second intervals for 2 minutes. In the other condition, the participant is asked to sit quietly in a room for 2 minutes. Every participant completes the two conditions twice, performing both conditions one in a dark room and also once in a lighted room.

The analyses mimic the analyses of the driving simulation study. Two mental alertness levels are selected: effortful processing and relaxed/bored. All seconds of data from all four conditions are coded 0 or 1, with both problem solving conditions coded '1' and both non-problem solving conditions coded '0.' Two sets of data are created, the original 1-second data and the averaged 5-second data. And, two analyses are done on each data set: linear discriminant function analysis and neural network classification. As before, the discriminant function analysis yielded a single discriminant function that was statistically significant for all individuals. The neural network had the same structure as that for the driving simulation study, i.e., a 3-layer network with 7 hidden units.

The eye tracking metrics accurately identify the mental alertness levels of effortful processing and relaxed/bored. In this example, the procedures outlined correctly identified the condition in which the second occurred approximately 75% of the time or more.

A third example is a visual search task. The mental alertness level of interest is fatigue. The task is a neuropsychological visual search task in which many representations of one letter were displayed in scrambled orientation on the computer screen. The target was the letter in the left-facing orientation ('C,' 'E,' 'G,' or 'S'). A participant responds with key press 'Yes' if target is present and 'No' if target is absent. Each task run presents 104 trials, with some containing a single target and others containing no targets. Each trial presents a random arrangement of the stimuli. At the end of each task run, participants provide a subjective estimate of fatigue on a 10-point scale.

The eye tracking metrics correctly identify the mental alertness level of fatigue. The discriminant function analysis results in correct classification of 76% of all seconds for 1-second data and correct classification of 84% for 5-second data. The neural network results were similar. The network accurately classifies 81% of the 1-second data and 88% of the 5-second data.

Another example of selecting a task, selecting mental proficiency levels of interest, collecting data, computing metrics, and determining an operator's mental proficiency level involves a simulated air traffic control task. Using a simulation program presented on a computer monitor, individuals complete a tutorial about how to interact with incoming and outgoing aircraft in a simulated environment of air traffic control. Each individual is then tested on the task in its simplest configuration and on several other configurations. The testing session lasts approximately 3 hours, with each task taking just over 11 minutes to complete. At the end of testing on day one, the individual is expected to be competent and able to perform the task with relatively few errors. Two days later, the individual returns for additional testing on the same tasks using slightly altered stimuli.

This example looks at two distinct levels of mental proficiency: novice or untrained (the first task on day one performed immediately after the tutorial) and competent or trained (the corresponding first task on day two performed after a few minutes of warm up). To test whether the observed data reflects two distinct levels, all seconds of performance are given a binary code, with the seconds during the novice only episodes coded '0' and the seconds during the competent episodes coded '1.' The data from each episode are combined for each individual and are analyzed to determine whether the eye metrics reliably estimate the level of mental proficiency coding.

As before, both data sets can be analyzed in two ways: first with a linear discriminant function and second with a nonlinear, backpropagation neural network analysis. With only two categories of classification, the discriminant function analysis can yield a single function which was statistically significant in all cases. The neural network is a 3-layer network with 7 inputs (the metrics), 5 hidden units, and 2 output units (novice and competent). Separate analyses using each classification technique can be done for each participant.

The results show that the analysis based on eye tracking data accurately describes the level of mental proficiency of the individual. On the basis of each second of data, the level of mental proficiency can be correctly predicted as untrained (novice) or trained (competent) by the nonlinear analysis more than 84% of the time and by the linear discriminant analysis over 82% of the time.

Figure 4:
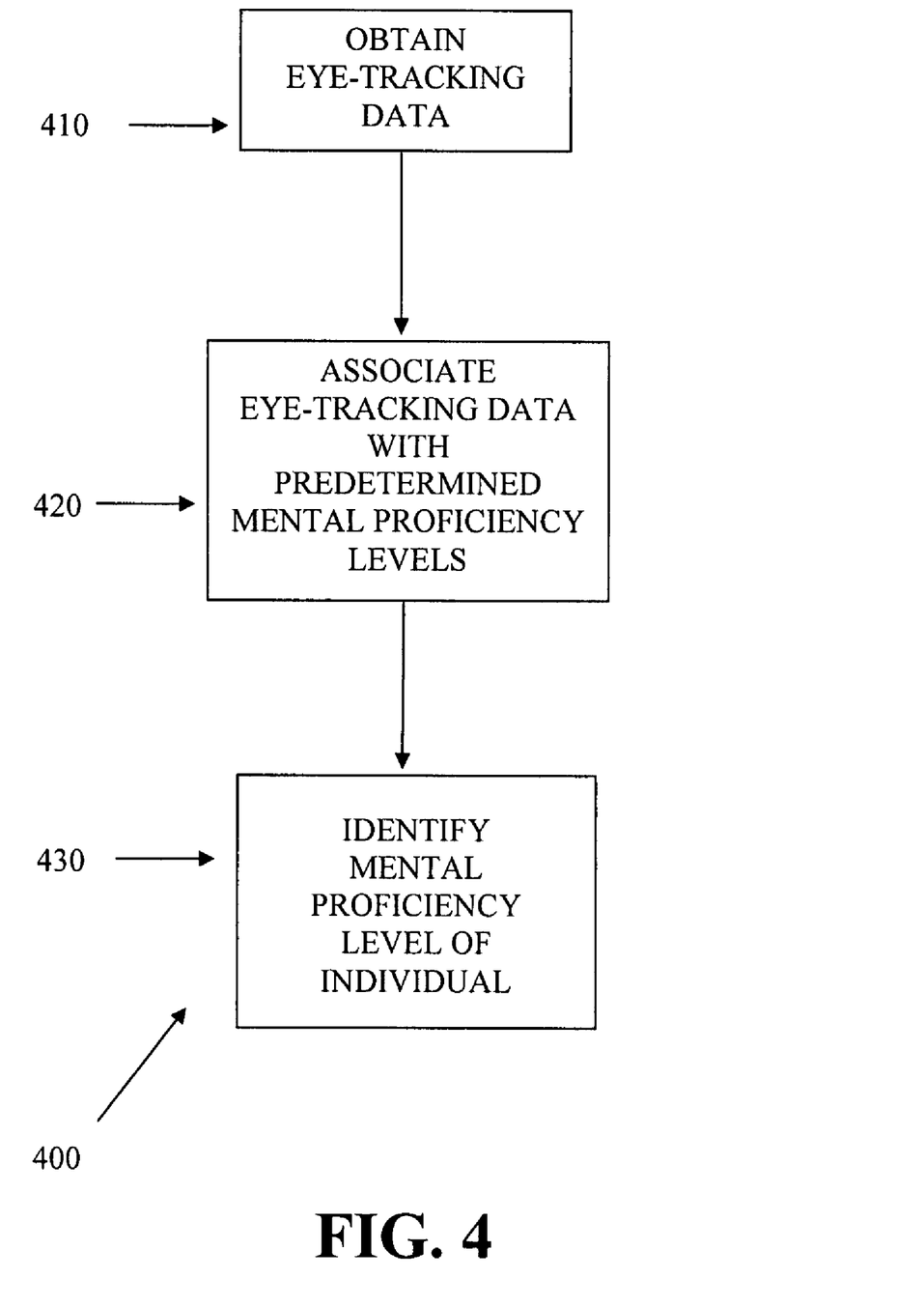
FIG. 4 is a process flow diagram illustrating an identification of a mental proficiency level.

FIG. 4 is a process flow diagram 400 showing the processes involved in identifying the mental alertness or mental proficiency level or levels of an individual. While monitoring an individual's pupils, eye tracking data characterizing, for example, pupil dilation and point of gaze are obtained 410. These data, after analysis, are then associated with a collection of predetermined mental alertness levels 420, for example, obtained from empirical testing of individuals as described above. Once the data are analyzed and associated with one or more predetermined levels, the one or more mental alertness or mental proficiency levels of the individual of interest is identified 430.

Various implementations of the systems and techniques described herein may be realized in digital electronic circuitry, integrated circuitry, specially designed ASICs (application specific integrated circuits), computer hardware, firmware, software, and/or combinations thereof. The various implementations may include one or more computer programs that are executable and/or interpretable on a programmable system including at least one programmable processor, which may be special or general purpose, coupled to receive data and instructions from, and to transmit data and instructions to, a storage system, at least one input device, and at least one output device.

The computer programs (also known as programs, software, software applications, or code) may include machine instructions for a programmable processor, and may be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the systems and techniques described here), or any combination of such back-end, middleware, or front end components. The components of the system may be interconnected by any form or medium of digital data communication (e.g., a communication network). Examples of communication networks include a local area network ("LAN"), a wide area network ("WAN"), an intranet, the Internet, and wireless networks, such as a wireless WAN.

The computing system may include clients and servers. A client and server are generally remote from each other and typically interact through a communication network. The relationship of client and server arises by virtue of computer programs running on the respective computers and having a client-server relationship to each other.

A number of variations of the subject matter described herein have been described. Nevertheless, it will be understood that various modifications may be made without departing from the scope of the subject matter described herein.

What is claimed is:

1. A method comprising:
obtaining eye tracking data characterizing pupil dilation and point of gaze for an individual;
associating the data with one or more of a plurality of predefined mental proficiency levels, the predefined mental proficiency levels being derived from eye tracking data obtained from a plurality of individuals performing a substantially identical task, the plurality of predefined mental proficiency levels being generated by: providing a controlled setting characterized by one or more mental proficiency levels, subjecting one or more than one test individuals engaged in the task to the controlled setting, obtaining eye tracking data from the test individuals, performing calculations on the eye tracking data, and modeling the eye tracking data to describe the one or more mental proficiency levels;
identifying the associated predefined mental proficiency level to enable notification of the associated predefined mental proficiency level.

2. The method of claim 1, further comprising: performing a discriminant function analysis of the eye tracking data.

3. The method of claim 1, further comprising: performing a nonlinear classification analysis of the eye tracking data.

4. The method of claim 1, further comprising: selecting a defined job, task, or activity for the individual to participate in.

5. The method of claim 4 wherein the defined job, task, or activity is selected from a group comprising: driving a vehicle; using a vehicle driving simulator; undertaking problem solving; or performing a visual search task.

6. The method of claim 1, wherein the eye tracking data is selected from a group comprising pupil size, eyelid opening and closing speed, vertical eyelid separation distance, vertical location of the pupil, or horizontal location of the pupil.

7. The method of claim 1, wherein
the eye tracking data are subjected to an analysis comprising one or more of:
calculating an Index of Cognitive Activity (ICA);
calculating a blink rate;
calculating a movement of the pupil in a horizontal and in a vertical plane; and
calculating a divergence of the horizontal location of the pupil.

8. The method of claim 1, wherein
the mental proficiency level is selected from a group comprising: expert, intermediate, and novice.

9. The method of claim 1, wherein the data collection and analysis occur in real time.

10. The method of claim 1, wherein the data analysis is performed on pre-exsiting data.

11. The method of claim 1, wherein the monitoring of pupils occurs at a frequency of up to about 1000 observations per second.

12. The method of claim 1 further comprising: monitoring eyes of one or more individuals.

13. The method of claim 1 further comprising: recording the eye tracking data.

14. The method of claim 1 further comprising: storing the eye tracking data.

15. The method of claim 1 further comprising: reporting the mental proficiency level of the one or more individuals.

16. The method of claim 15, further comprising: alerting a third party to the mental proficiency level of the individual.

17. The method of claim 15, further comprising: providing the individual with feedback identifying the mental proficiency level.

18. A method comprising:
obtaining eye tracking data characterizing pupil dilation and point of gaze for each eye of an individual;
calculating metrics based on the data comprising: index of cognitive activity, blink rate, rate of pupil movement, rate of change of point of gaze, and divergence between the point of gaze for each eye;
associating the metrics with one or more of at least two mental proficiency levels, the mental proficiency levels being derived from eye tracking data obtained from a plurality of individuals performing a substantially identical task in a controlled setting; and
identifying the associated predefined mental proficiency level to enable notification of the associated predefined mental proficiency level.

19. An apparatus comprising:
means for obtaining eye tracking data characterizing pupil dilation and point of gaze for an individual;
means for associating the eye tracking data with one or more of a plurality of predefined mental proficiency levels, the predefined mental proficiency levels being generated by providing a setting characterized by one or more mental proficiency levels, subjecting a plurality of test individuals engaged in a task to the setting, obtaining eye tracking data from the test individuals, performing calculations on the eye tracking data, and modeling the eye tracking data to describe the one or more mental proficiency levels; and
means for identifying the associated predefined mental proficiency level to enable notification of the associated predefined mental proficiency level.

20. A method comprising:
obtaining eye tracking data characterizing pupil dilation and point of gaze for an individual;
subjecting the eye tracking data to an analysis comprising one or more of:
 calculating an Index of Cognitive Activity (ICA);
 calculating a blink rate;
 calculating a movement of the pupil in a horizontal and in a vertical plane; and
 calculating a divergence of the horizontal location of the pupil;
associating the analyzed eye tracking data with one or more of a plurality of predefined mental proficiency levels; and
identifying the associated predefined mental proficiency level to enable notification of the associated predefined mental proficiency level.

* * * * *